(12) United States Patent
Akui et al.

(10) Patent No.: US 6,582,358 B2
(45) Date of Patent: Jun. 24, 2003

(54) STEREOSCOPIC ENDOSCOPE SYSTEM

(75) Inventors: Nobuaki Akui, Tokyo (JP); Kazuo Banju, Tokyo (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/843,709

(22) Filed: Apr. 30, 2001

(65) Prior Publication Data

US 2002/0035310 A1 Mar. 21, 2002

(30) Foreign Application Priority Data

Sep. 12, 2000 (JP) ........................................ 2000-277050

(51) Int. Cl.⁷ .................................................. A61B 1/04
(52) U.S. Cl. ....................................................... 600/111
(58) Field of Search ................................. 600/111, 112, 600/166, 113, 175, 109, 117; 359/462, 464

(56) References Cited

U.S. PATENT DOCUMENTS

| | | | | |
|---|---|---|---|---|
| 4,862,873 A | * | 9/1989 | Yajima et al. ................. 348/45 |
| 4,924,853 A | * | 5/1990 | Jones, Jr. et al. ............... 128/6 |
| 5,527,263 A | * | 6/1996 | Zobel et al. ................. 600/166 |
| 5,588,948 A | * | 12/1996 | Takahashi et al. ........... 600/111 |
| 5,689,365 A | * | 11/1997 | Takahashi .................... 359/362 |
| 5,743,846 A | * | 4/1998 | Takahashi et al. ........... 600/166 |
| 6,066,090 A | * | 5/2000 | Yoon ............................ 600/113 |
| 6,471,642 B1 | * | 10/2002 | Igarashi ........................ 600/166 |
| 2002/0035310 A1 | * | 3/2002 | Akui et al. .................... 600/111 |
| 2002/0114071 A1 | * | 8/2002 | Igarashi ........................ 359/462 |

FOREIGN PATENT DOCUMENTS

JP           64-24215 A  *  1/1989  ............... 600/111

* cited by examiner

Primary Examiner—Noah P. Kamen
Assistant Examiner—Hyder Ali
(74) Attorney, Agent, or Firm—Armstrong, Westerman & Hattori, LLP

(57) ABSTRACT

A stereoscopic endoscope system includes a combined system of a stereoscopic endoscope unit and a camera unit. The stereoscopic endoscope unit has an insertion part and an observation part. The insertion part includes an objective lens and a relay lens in order from an object side, where the objective lens has a pair of first optical system and a second optical system which are arranged in parallel in an insertion direction, and a third optical system arranged in the insertion direction. The first optical system and the second optical system are for a stereoscopic vision observation, and the optical system has a viewing angle larger than that of the first and the second optical systems for observing a wider range than a that of the stereoscopic vision observation. The relay lens is arranged on the camera unit side of the objective lens.

21 Claims, 10 Drawing Sheets

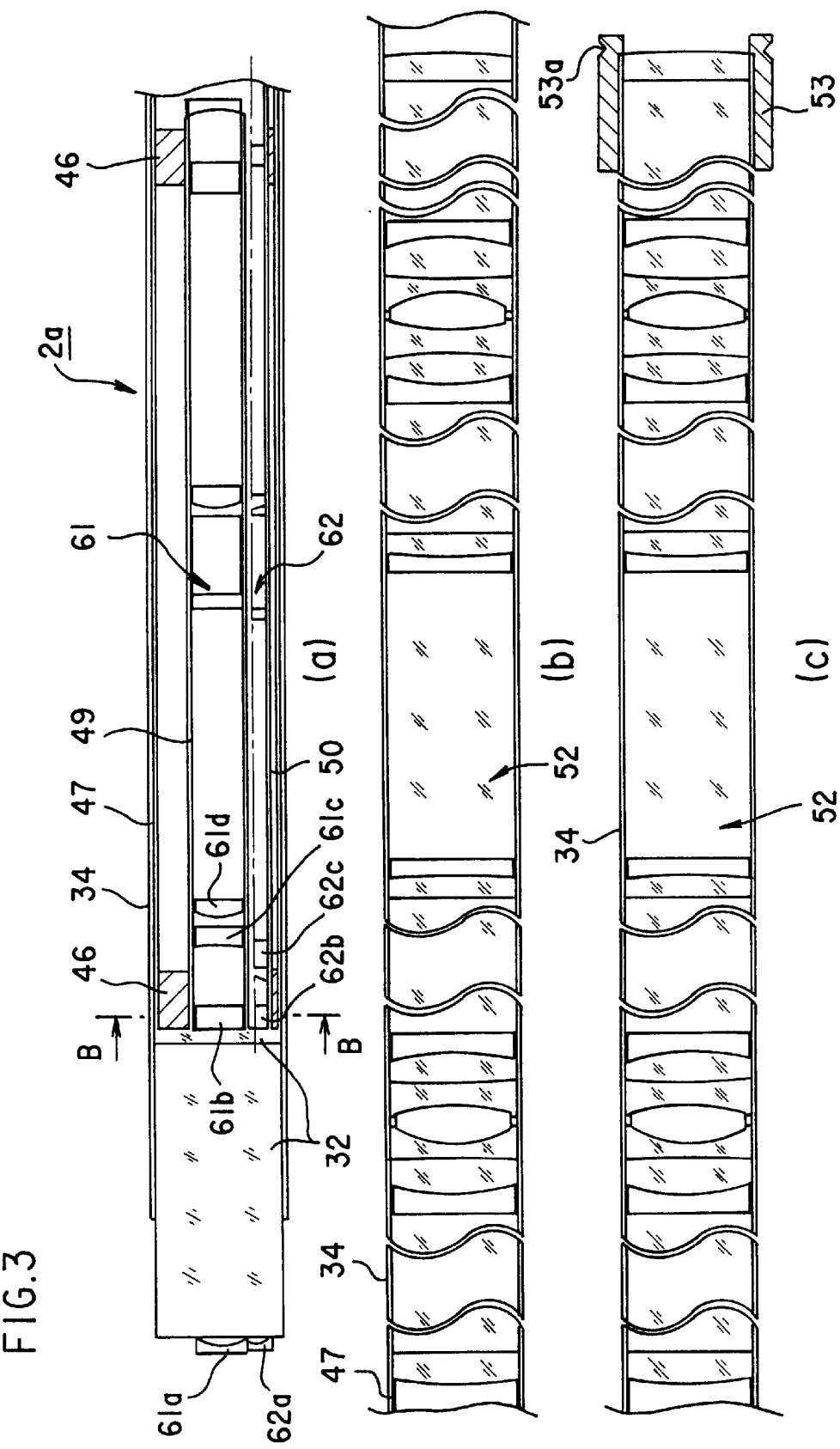

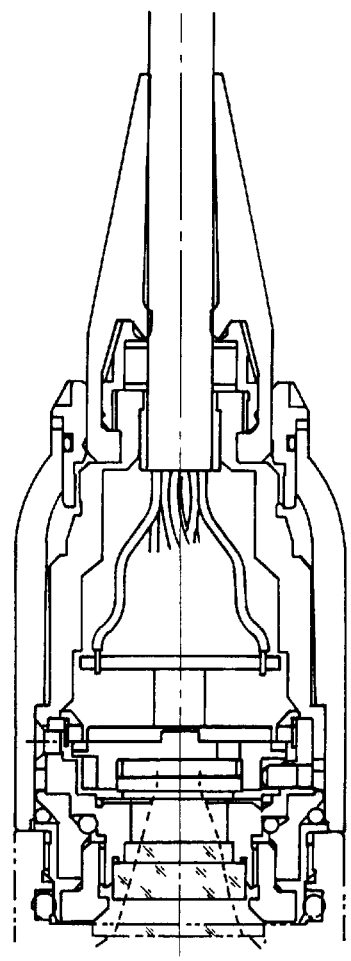
FIG.14
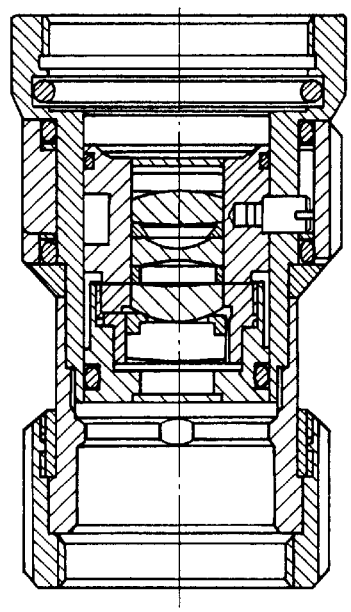

1

STEREOSCOPIC ENDOSCOPE SYSTEM

FIELD OF THE INVENTION

This invention relates to a stereoscopic endoscope system for observing an object in three dimensions. More specifically, it relates to a stereoscopic endoscope system in which a visual field range can be properly used for both cases of wide-angle and narrow angle view, without moving a lens or a whole endoscope apparatus forward or backward against an object.

BACKGROUND OF THE INVENTION

In general, a stereoscopic rigid endoscope has an objective optical system consisting of an objective lens which forms an object image, a transmission optical system consisting of a relay lens which transmits the object image, a pupil dividing means to divide the image transmitted by the transmitting optical system into right and left images, an eyepiece for observing the two images, and an image-formation optical system and a TV camera for photographing the divided images.

An operator may sometimes want to confirm treatment tools that are outside of the visual field range and the entire position relationship in the body while treating an affected region in the living body using the stereoscopic vision endoscope. If the visual field range of a stereoscopic endoscope is initially set at a narrow angle, it is necessary to zoom a lens toward a wide-angle side or to move the whole endoscope in order to observe treatment tools outside the visual field range and the entire position relationship. However, at this time, the treatment of the affected region must be interrupted causing the operator to lose his concentration on the surgery, thereby decreasing the efficiency of the surgery.

In this regard, in order for the operator to perform an exact and efficient surgery, it is necessary to treat under sufficient enlargement magnification in the same state of a narrow angle visual field range and observe not only the treatment tools located outside the visual field but also the entire position relationship, without moving the lens and the whole endoscope.

In an attempt to solve the above problems, it is conceivable to provide a plurality of objective lenses each having a different visual field range. However, this causes the outer diameter of an insertion part of the endoscope to become larger. Thus, in order to solve the above problems it is necessary to devise an improved optical system and new mechanical structure to incorporate the optical system correctly and efficiently into the endoscope device.

SUMMARY OF THE INVENTION

In view of the foregoing disadvantages inherent in the known types of prior art systems, the present invention solves the above-mentioned problems. Thus, it is an object of the invention to provide a stereoscopic endoscope system equipped with a new mechanical structure that can be used properly for both cases of wide-angle and narrow angle view, without moving a lens or the endoscope itself. This application claims benefit of Japanese Application No. 2000-277050, filed on Sep. 12, 2000, the contents of which are incorporated by this reference.

In order to achieve the aforementioned objects, in a first aspect of the present invention, a stereoscopic endoscope system includes a combined system of a stereoscopic vision endoscope unit and a camera unit, said system comprising: an insertion part and an observation part; said insertion part including an objective lens and a relay lens in order from an object side, said objective lens having a pair of first and second optical system s which are arranged in parallel in an insertion direction, and a third optical system arranged in the insertion direction, said first and second optical systems being optical systems for a stereoscopic vision observation, said third optical system having a viewing angle larger than that of the first and second optical systems for observing a wider range than that of the stereoscopic vision observation; and said relay lens arranged on the camera unit side of the objective lens.

The objects of the present invention are also achieved by providing a stereoscopic endoscope wherein the first optical system is inserted and fixed to a first tubular member, the second optical system is inserted and fixed to a second tubular member and the third optical system is inserted and fixed to a third tubular member.

The objects of the present invention are also achieved by providing a stereoscopic endoscope wherein the first to third optical systems are positioned by a position regulation member which supports both ends of the first to third optical systems at the object and the camera sides thereof, and the position regulation member is inserted and fixed to a fourth tubular member.

The objects of the present invention are also achieved by providing a stereoscopic endoscope, wherein said observation part includes an image formation optical system and an enlargement optical system, said image formation optical system and said enlargement optical system being arranged in the camera side of the relay lens, said image formation optical system and said enlargement optical system include a pair of image formation optical systems and a pair of enlargement optical systems, corresponding to the pair of first and second optical systems, and a single substance image formation optical system and a single substance enlargement optical system, corresponding to the third optical system, are arranged in the camera side of the relay lens.

The objects of the present invention are also achieved by providing a stereoscopic endoscope wherein the pair of the image formation optical systems and the single substance enlargement optical system are respectively inserted in a lens frame, wherein the lens frame has an adjusting mechanism so that a position can be adjusted in a direction perpendicular to a direction of an optical axis.

The objects of the present invention are also achieved by providing a stereoscopic endoscope wherein said adjusting mechanism adjusts the optical axis by screwing a plurality of screws into a v-shaped slot provided on a periphery of the lens frame.

The objects of the present invention are also achieved by providing a stereoscopic endoscope wherein said observation part has two parallelogram prisms arranged to correspond to the pair of first and second optical systems, respectively, so that an optical path can be extended on the camera side of the relay lens, and the image formation optical system and the enlargement optical system are arranged on the camera side of the parallelogram prism.

The objects of the present invention are also achieved by providing a stereoscopic endoscope wherein the single substance image formation optical system is integrally arranged in a space which is formed by cutting out a marginal part of each of the two parallelogram prisms, and a holder is arranged to fix the two parallelogram prisms and the single substance image formation optical system together, and the holder has an adjusting mechanism so that a position can be adjusted in a surface vertical to the insertion direction which is the direction of optical axis.

The objects of the present invention are also achieved by providing a stereoscopic endoscope wherein the stereoscopic vision endoscope unit includes an insertion part, an observation part, and a light guide, wherein the light guide is built in and arranged in a section from the object side end of the objective lens to the observation part, and in a space between an outer side sheath of the stereoscopic vision endoscope unit and the objective and relay lenses.

The objects of the present invention are also achieved by providing a stereoscopic endoscope wherein said light guide is ramified into a pair at an observation part terminal.

The objects of the present invention are also achieved by providing a stereoscopic endoscope wherein said light guide is divided into a pair of light source light guide cables which tie the observation part and a light source, and the pair of light source light guides are detachablly mounted to the light guide.

The objects of the present invention are also achieved by providing a stereoscopic endoscope wherein the light guide is built in a section from the object side end of the objective lens to the observation part and in a space between the outer side sheath of the stereoscopic vision endoscope unit, and the objective and the relay lenses, in a position near the third optical system.

The objects of the present invention are also achieved by providing a stereoscopic endoscope wherein the camera unit includes an a adapter and a camera head, wherein the adapter includes a pair of adapter image formation optical systems and an adapter image formation optical system of a single substance corresponding to the pair of enlargement optical systems and the single substance enlargement optical system.

The objects of the present invention are also achieved by providing a stereoscopic endoscope wherein the pair of the adapter image formation optical systems is inserted into a image formation lens frame, wherein the image formation lens frame includes a focus moving mechanism for focus adjustments, and when the image formation lens frame moves, the pair of the adapter image formation optical systems moves simultaneously.

The objects of the present invention are also achieved by providing a stereoscopic endoscope wherein the focus moving mechanism of the pair of the adapter image formation optical systems includes a worm shaft which causes movement in direction of an optical axis, and a rotation prevention shaft which prevents rotation of the image formation lens frame in connection with the rotation of the worm shaft.

The objects of the present invention are also achieved by providing a stereoscopic endoscope wherein said focus moving mechanism of the pair of the adapter image formation optical systems having a guide shaft provided along a transfer shaft and a rotation roller, which rotates and moves in contact with the guide shaft, arranged in the image formation lens frame, in order to prevent rotation resulting from the ricketiness of the rotation prevention shaft and the image formation lens frame.

The objects of the present invention are also achieved by providing a stereoscopic endoscope wherein the rotation roller is pressed down on the guide shaft by the force of a spring.

The objects of the present invention are also achieved by providing a stereoscopic endoscope wherein said camera head includes a pair of solid image pick-up elements, corresponding to the pair of the adapter image formation optical systems, and a solid image pick-up element corresponding to the adapter image formation optical system of the single substance.

The objects of the present invention are also achieved by providing a method for adjusting or assembling a stereoscopic endoscope system, comprising at least the following steps: (A) fixing the position of a plurality of objective lenses in an insertion part, and a relay lens; (B) forming a stereoscopic endoscope unit by combining an observation part with the insertion part; (C) fixing the position of an image formation optical system and an enlargement optical system built-in in the observation part; (D) combining a camera unit with the stereoscopic endoscope unit; and (E) fixing the position of an adapter and a camera head built-in in the camera unit.

The objects of the present invention are also achieved by providing a method for adjusting or assembling a stereoscopic endoscope system, wherein said step (A) includes the following steps, respectively inserting a plurality of the objective lenses in a plurality of object tubular members and fixing it, a plurality of the object tubular members fixes the relative position of a plurality of the object optical systems by a pair of position regulation members which support the both ends of the object and the camera thereof, inserting the position regulation member into an insertion tubular member and fixing it, fixing the relay lens in contact with the camera side of the insertion tubular member; said step (B) comprising of the following step at least, combining the observation part with the insertion part, and fixing a rotation position centering around the insertion direction; said step (C) comprising of the following step at least, performing the positioning control of the direction of an optical axis of the image formation optical system and positioning control in surface vertical to an optical axis, and fixing; said step (D) comprising of the following step at least, combining a camera unit with the stereoscopic endoscope unit, and fixing a rotation position centering around an insertion direction; said step (E) comprising of the following step at least, fixing by performing the positioning control of the direction of an optical axis of the adapter and the camera head, and positioning control in surface vertical to an optical axis.

BRIEF DESCRIPTION OF DRAWINGS

FIG. 2(b) is an expanded sectional view of the side of the end of the insertion part of FIG. 2(a).

FIG. 3(a) is a sectional drawing of the side of the end in which the object optical system of the observation optical system of the insertion part of the stereoscopic endoscope of FIG. 2 is accommodated.

FIG. 3(b) is a sectional drawing of an observation optical system part where the transmittance optical system exists.

FIG. 3(c) is a sectional drawing of the side of the observation part of the observation optical system where the transmittance optical system exists.

FIG. 14 shows a single adaptor image formation optical system and a single solid image pick-up element connected to a single observation optical system.

DETAILED DESCRIPTION OF THE PREFERRED EMBODIMENT

With reference to the accompanying drawings, examples of stereoscopic endoscope system illustrating the embodiments of the present invention, will be explained hereinafter.

Figure 1:
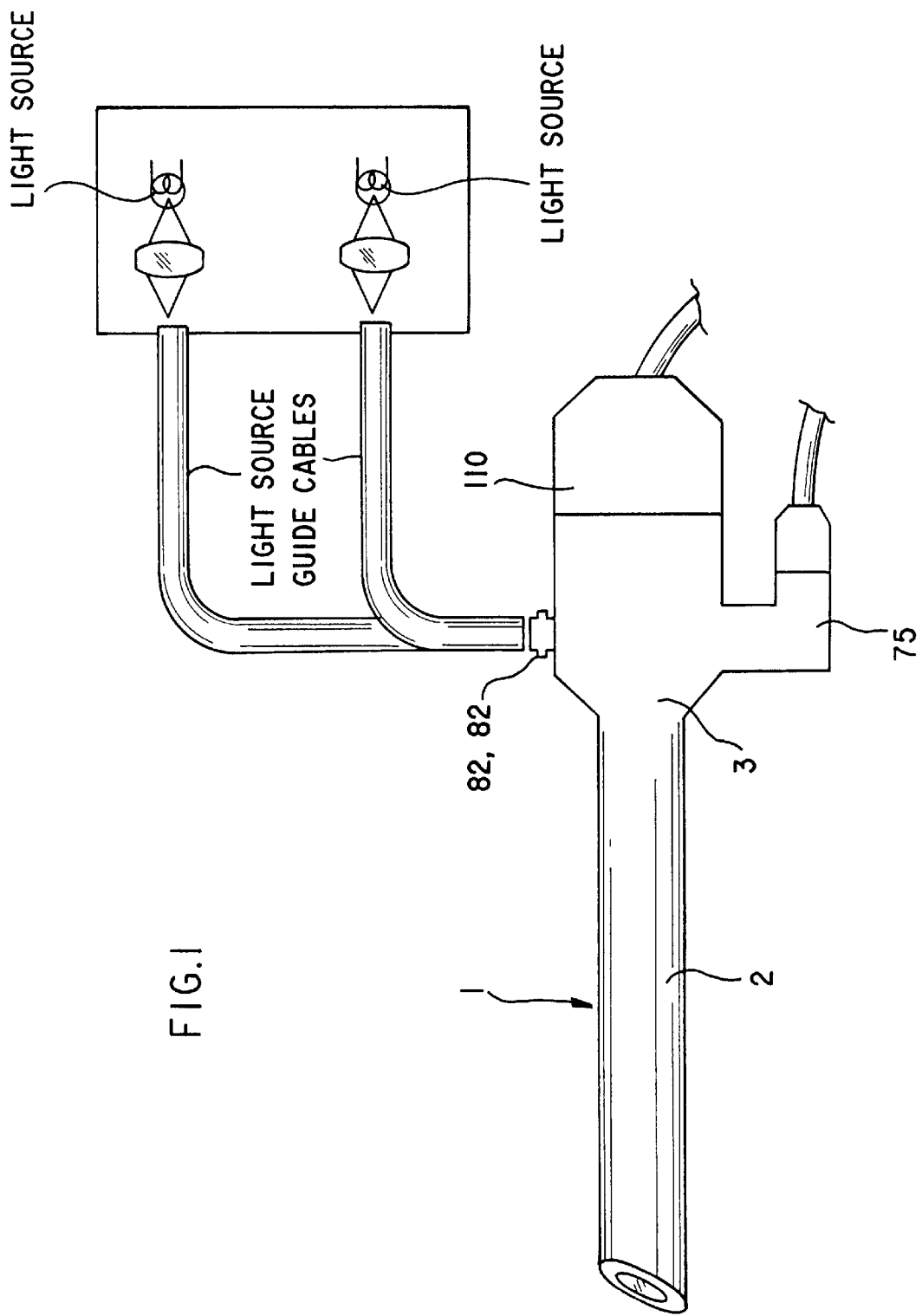
FIG. 1 is a schematic view of a stereoscopic endoscope system according to the present invention.

FIG. 1 is a schematic view of a stereoscopic endoscope system of the present invention employing a combined system of a stereoscopic vison endoscope unit 1 and a camera unit. A pair of light guide connectors 82, 82 are provided which receive illumination light from two light sources are provided. Detachably mounted to the pair of light guide connectors 82, 82 are a pair of light source guide cables through which the illumination light is transmitted from a light source.

Figure 2A:
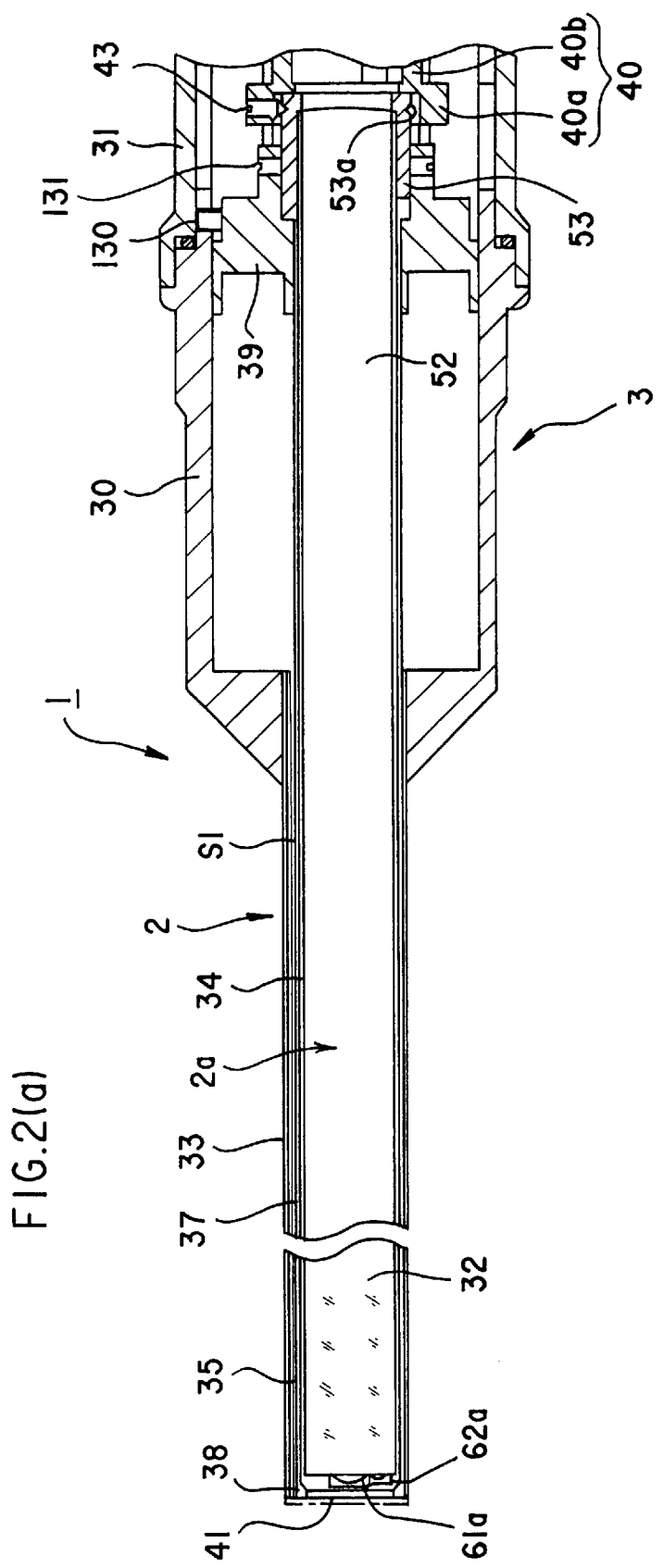
FIG. 2(a) is a sectional view of the side of the insertion part of a stereoscopic vision endoscope according to an embodiment of the present invention.

FIG. 2(a) is a sectional view of the side of the insertion part of a stereoscopic vision endoscope according to an embodiment of the present invention. FIG. 2(b) is an expanded sectional view of the side of the end of the insertion part of FIG. 2(a).

The stereoscopic vision endoscope unit 1 consists of an insertion part 2 and an observation part 3 connected to a base end side of the insertion part 2. The insertion part 2 consists of a tubular inner side sheath 37 in which an optical system 2a in the insertion part passes through and is arranged, and a tubular outer side sheath 33 in which the inner side sheath 37 passes through and is arranged.

Figure 4:
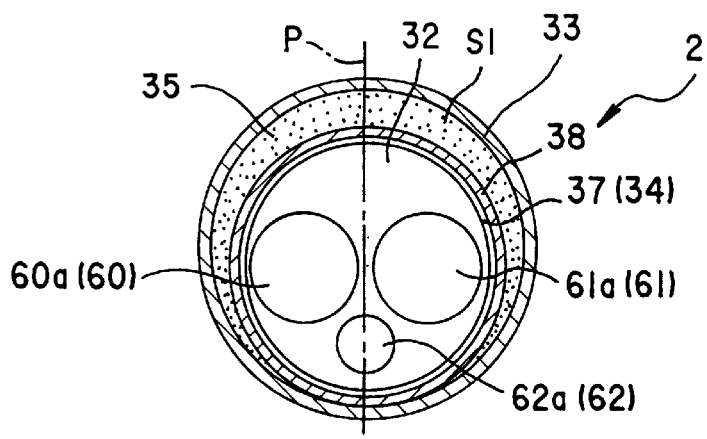
FIG. 4 is a sectional drawing along line A—A line of FIG. 2(b).

The longitudinal center axis of the inner side sheath 37 and the longitudinal center axis of the outer side sheath 33 are eccentric. From this eccentricity, a space S1 with a cross-sectional shape of a falcate is formed between sheaths 33 and 37 for the full length of sheaths 33 and 37, as shown in FIG. 4. That is, space S1 of this falcate has a larger cross section in the upper side of the diagram and becomes gradually smaller as it goes to the lower part of the diagram.

Figure 5:
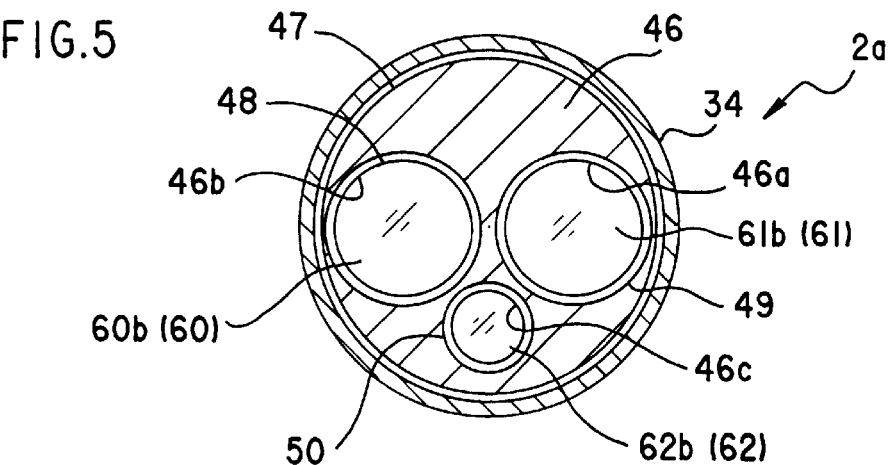
FIG. 5 is a sectional drawing along line B—B line of FIG. 3(a).
Figure 6:
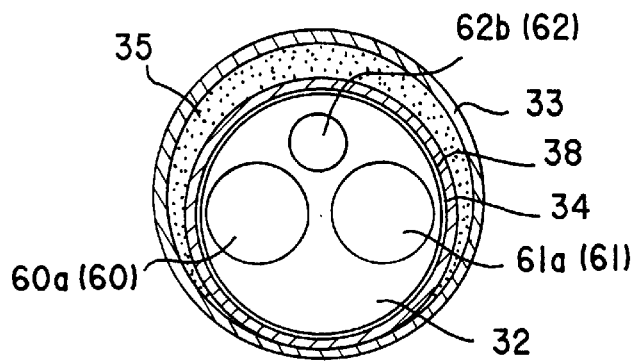
FIG. 6 is a sectional drawing relating to a modification of FIG. 4.
Figure 7:
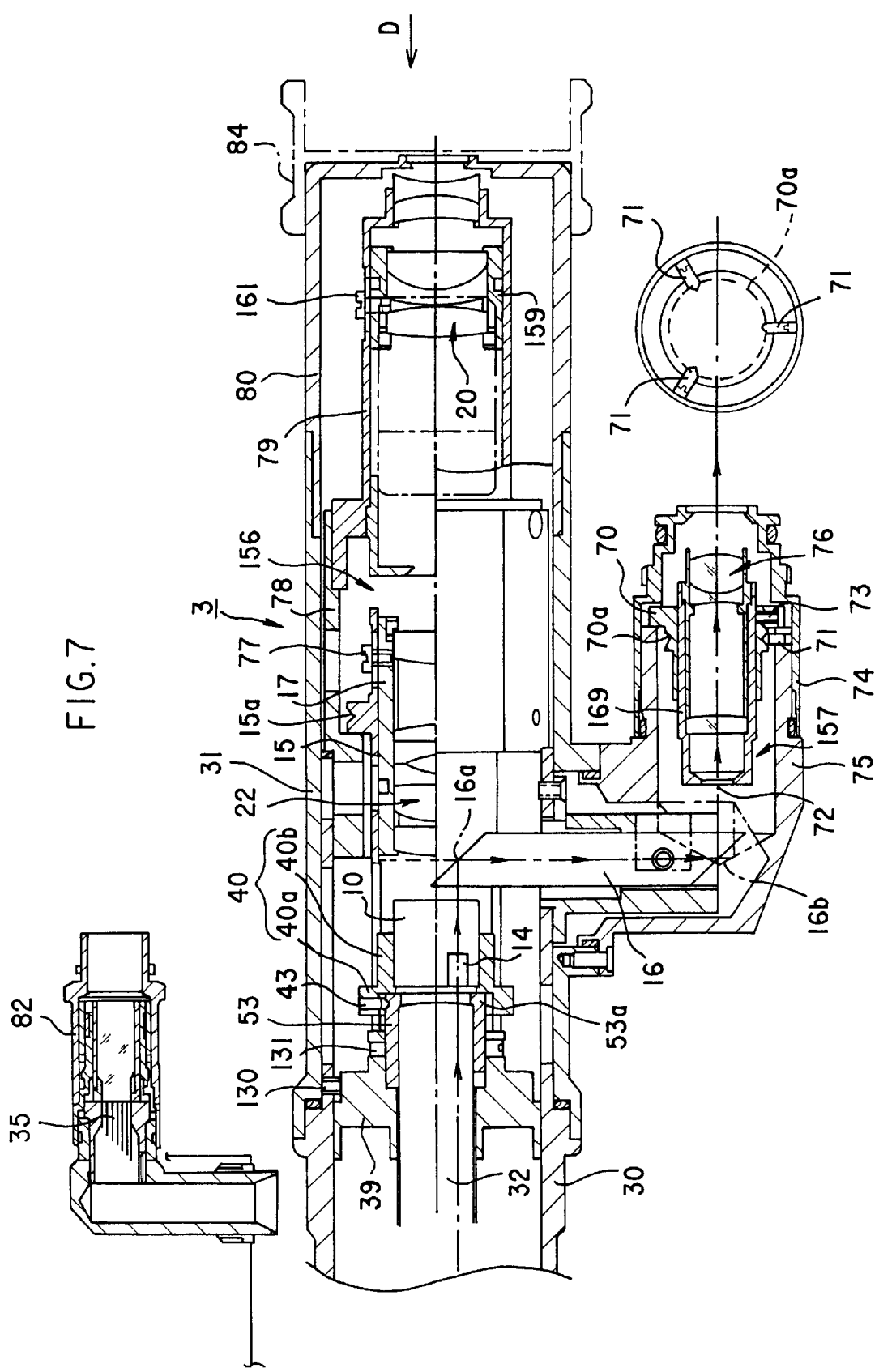
FIG. 7 is a cross-sectional view of the observation part of the stereoscopic vision endoscope of FIG. 2(a).
Figure 8:
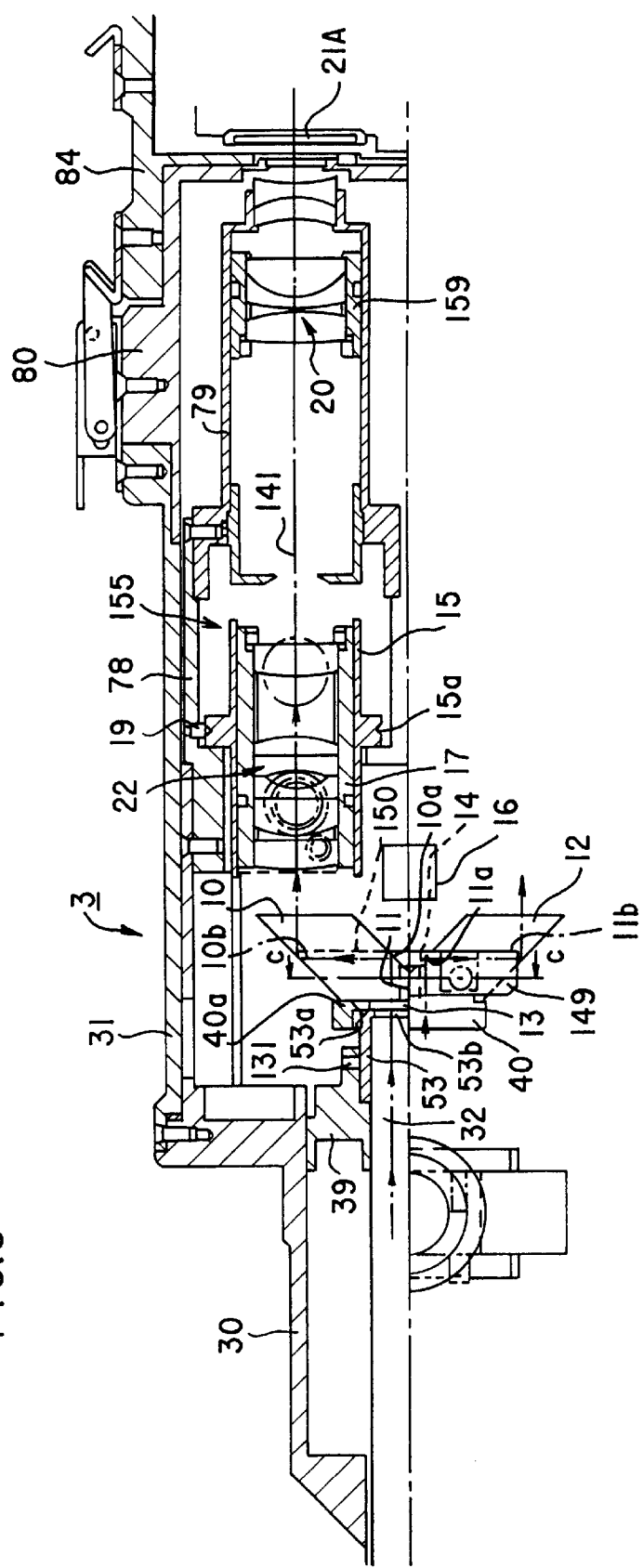
FIG. 8 is a cross-sectional view of the observation part of the stereoscopic vision endoscope of FIG. 2(a).

In the space S1, a light guide 35 for transmitting an illumination light is filled and built-in. In addition, a cylindrical leading end part material 38 is provided at the outside edge of the inner side sheath 37. A cover glass 41 is held at the end of the leading end part material 38. As shown in FIGS. 4–6, the observation optical system accommodated in the inner side sheath 37 has first and second object optical systems 60 and 61, of a right and left pair having a observation range, and a third object optical system 62 for observing, at the same time, a range outside the observation range without moving a lens or the endoscope itself.

Moreover, the observation optical system has one common transmission optical system 52 for batch transmission of an image from the first to the third object optical systems 60, 61 and 62.

The first object optical system 60 includes several objective lenses 60a 60b . . . , which form an object image, and is accommodated in a first tubular member 48 prolonged along the longitudinal direction at the end of the insertion part 2.

The second object optical system 61 includes several objective lenses 61a, 61b, 61c and 61d, which form an object image, and is accommodated in a second tubular member 49 prolonged in parallel to the first tubular member 48.

The third object optical system 62 includes several objective lens 62a, 62b and 62c . . . , and has an outer diameter smaller than the first and the second object optical systems 60 and 61. The third object optical system 62 is accommodated in a third tubular member 50 having a diameter smaller than the diameters of the first and second tubular members 48 and 49 and prolonged in parallel to the first and second members 48 and 49.

In the drawings, reference numeral 32 depicts the lens that is used in common for the three object optical systems 60, 61, and 62.

Moreover, the transmission optical system 52 exists at the base end side of the three object optical systems 60, 61, and 62.

The transmission optical system 52 includes several relay lenses. In order to optically position to object optical systems 60, 61, and 62, the ends of the first to third tubular members 48, 49 and 50 are fixed to a disc-shaped position regulation member 46, which is itself fixed to a fourth tubular member 47. The fourth tubular member 47 is inserted into a fifth tubular member 34.

The tubular members 48, 49, and 50 are mechanically positioned at the leading end part of the fifth tubular member 34. In this case, the position regulation member 46 has three through-holes 46a, 46b, and 46c to which the edge part of the tubular members 48, 49, and 50 are inserted, respectively.

Moreover, the fourth tubular member 47 functions as a spacer which maintains the space of the object optical systems 60, 61, and 62 and the transmittance optical system 52. In addition, as shown in FIG. 4, the first and the second object optical systems 60 and 61 are disposed on both sides of a vertical flat surface P which passes along the longitudinal center axis of the insertion part 2, and on the upper side of the insertion part 2 when compared with the third object optical system 62.

Moreover, the fill of the light guide 35 exists to a lesser extent at the bottom, as shown in FIG. 4, so that the third object optical system 62 may straddle the vertical flat surface P. However, in order to impart much more illumination light to the third object optical system 62, the position relationship shown in FIG. 4 may be reversed. The third object optical system 62 may be located at the upper side where many fills of the light guide 35 exists, as shown in FIG. 6.

Next, the observation part 3 is explained, referring FIGS. 2(a), 2(b), 7 and 8. The observation part 3 has a first cover 30 connected to the base end part of the outer side sheath 33, as shown in FIG. 2(a).

A cylindrical mounting member 39 is fixed to the base end part of the transmission optical system 52. The mounting member 39 is attached to the first cover 30 and is adjustable in the Z direction through screw 130. Moreover, the base end part of the transmission optical system 52 is mounted to a cylindrical connection member 53, wherein more of the cylindrical connection member 53 exists at the base end side of the transmission optical system 52 than that of the mounting member 39. The connection member 53 is adjusted in the Z direction through screw 131, thereby being thrust into the mounting member 39.

Figure 9:
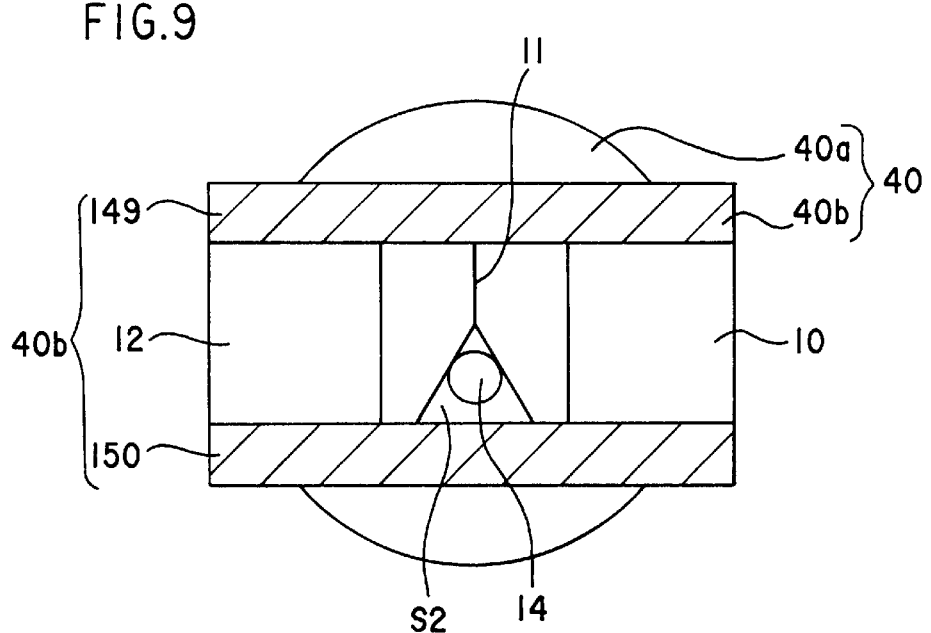
FIG. 9 is a sectional drawing along line C—C of FIG. 8.

Moreover, the connection member 53 is attached to a holder 40 which holds a pair of prisms 10 and 12. As shown in FIG. 9, the holder 40 consists of a connector 40a having a cylindrical shape which is connected to the connection member 53, and a rectangle-shaped retainer 40b having a pair of plate-like members 149, 150, for securing and supporting the pair of prisms 10 and 12. Moreover, each of the prisms 10 and 12 has the shape of a rough parallelogram and is arranged in contact with the flat surface part 11.

Next, an edge is cut off and a triangular space S2 is formed on the bottom of a contact part. Inside of space S2, a cylinder shaped single substance image formation optical system 14 is fixed by bonding it with the surfaces of each prisms 10 and 12.

The function of the pair of prisms 10 and 12 is now explained.

The image formed by the first and second object optical systems 60 and 61 is transmitted through the common transmission optical system 52. The image is then divided into right and left images by the pair of prisms 10 and 12 and then lead to a pair of observation optical systems 155, 156, respectively. In other words, the pair of prisms 10 and 12 function as a pupil dividing means.

Moreover, the single substance image formation optical system 14 leads the transmitted image to a single enlargement optical system 157, discussed intra, through the transmission optical system 53 from the third object optical system 62.

The holder 40 is mounted on the connection material 52 and is adjustably in an XY plane through a screw 43 by equal angle intervals in a peripheral direction. Specifically, a v-shaped groove 53a is formed over the whole circumference of the connection material 53. The end of the thread screw 43 is thrust into the connector 40a of the holder 40 to connect with the v-shaped groove 53a.

A alignment of the pair of observation optical systems 155, 156 and the single enlargement optical system 157, which corresponds to the prisms 10 and 12 and the single substance image formation optical system 14 held at the holder 40, respectively, is performed collectively. Moreover, the holder 40 can fix the direction of an optical axis.

Each of the observation optical systems 155, 156 include an image formation optical system 22 which performs a focus adjustment, and an enlargement optical system 20 which determines a multiplying factor. These optical systems 22 and 20 are arranged in a third cover 80 which is connected to a second cover 31, wherein the second cover 31 is in a watertight manner connected to the first cover 30 by a screw, etc.

The image formation optical system 22 consists of a plurality of lenses and is held by a lens frame 17 is inserted into a cylindrical holding member 15. The lens frame 17 can be moved in the direction of the optical axis toward a holding member 15 so that the direction (Z direction) of the optical axis of the image formation optical system 22 can be controlled. And, the position in the axial direction is fixed by screw 77.

Moreover, the holding member 15 is adjustable in the XY plane with respect to the first cover 30 and an integral fixing member 78 through a screw 19 at equal angle intervals in a peripheral direction. Specifically, groove 15a having a v-shaped is formed over the whole circumference of the holding member 15, and the end of the thread screw 19 is thrust into the fixing member 78 thereby connecting it to the v-shaped groove 15a. Further, by adjusting the screw 19 using the clearance of v-shaped groove 15a, the position of the holding member 15 can be adjusted in the XY plane, and the centering of the image formation optical system 22 held through the lens frame 17 at the holding member 15 can be performed.

Moreover, the enlargement optical system 20 consists of a plurality of lenses held by a first lens frame 159, and a plurality of lenses held by a second lens frame 79. The first lens frame 159 is inserted to the second lens frame 79. The second lens frame 79 is connected to the fixing member 78. The first lens frame 159 can be moved in the direction of the optical axis toward the second lens frame 79 so that the position in the direction (Z direction) of the optical axis of the enlargement optical system 20 can be controlled. The position of the axial direction is fixed by screw 161.

Moreover, the observation optical system 157 has a single enlargement optical system 76 which includes a plurality of the lenses and a prism 16 which receives light from a lens 14 and leads it to the optical system 76. The prism 16 and the single enlargement optical system 76 are arranged inside a fourth cover 75 which is connected in a watertight manner to the second cover 31 by a screw, etc., and a fifth cover 74 which is connected in a watertight manner to the fourth cover 75. The single enlargement optical system 76 is held by a lens frame 169. The lens frame 169 is inserted into a cylindrical holding member 70. The lens frame 169 can be moved in the direction of the optical axis toward a holding member 70 so that the direction (Z direction) of the optical axis of the single enlargement optical system 76 can be controlled. The position of the axial direction is fixed by screw 73.

The holding member 70 is adjustable in the XY plane with respect to the fourth cover 75 through a screw 71 at equal angle intervals in a peripheral direction. Specifically, groove 70a having a v-shaped is formed over the whole circumference of the holding member 70, and the end of the thread screw 71 is thrust into the fourth cover 75 thereby connecting it to the v-shaped groove 70a. The single enlargement optical system 76 held through the lens frame 169 at the holding member 70 is centered by adjusting the position of the holding member 70 in the XY plane by adjusting the screw 71 using the clearance of the v-shaped groove 70a.

Figure 10:
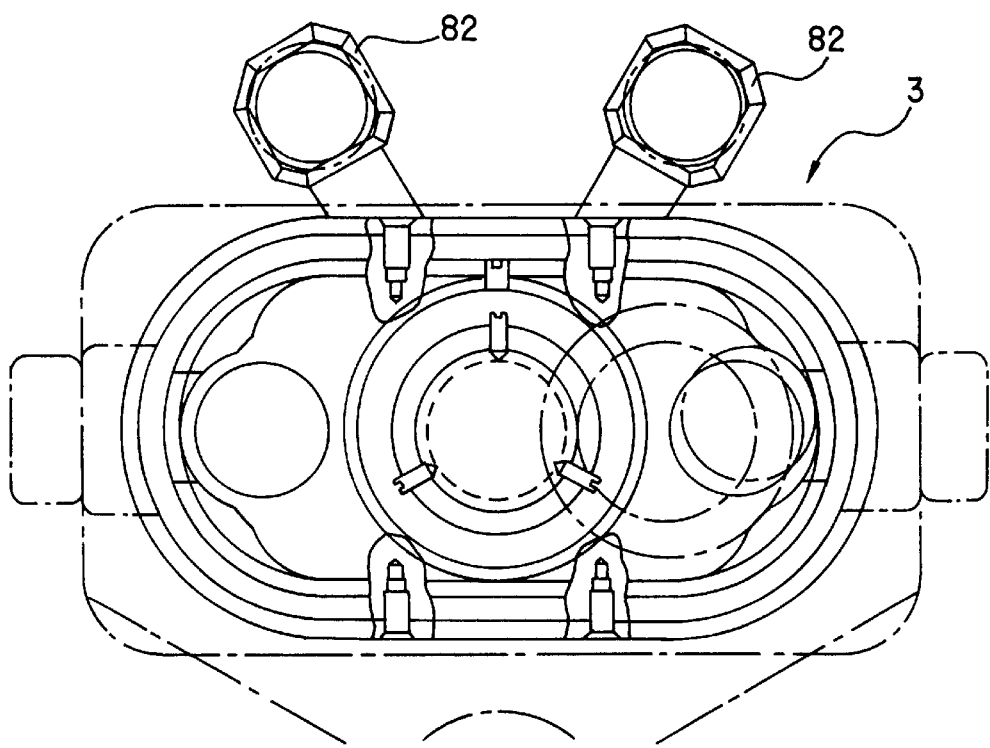
FIG. 10 is a sectional drawing in the direction of arrow D of FIG. 7.

As shown in FIG. 10, at the observation part 3, a pair of light guide connectors 82, 82 which receive illumination light from two light sources are provided. Detachably mounted to the pair of light guide connectors 82, 82 are a pair of light source guide cables through which the illumination light is transmitted from a light source (see FIG. 1). Inside of each of the light guide connectors 82 and 82, the base end part of the light guide 35 is prolonged toward the insertion part 2 (see FIG. 7). The light guide 35 is prolonged into the insertion part 2 passing through between the first cover 30 and the inner side sheaths 37 from the light guide connectors 82, 82.

Figure 11:
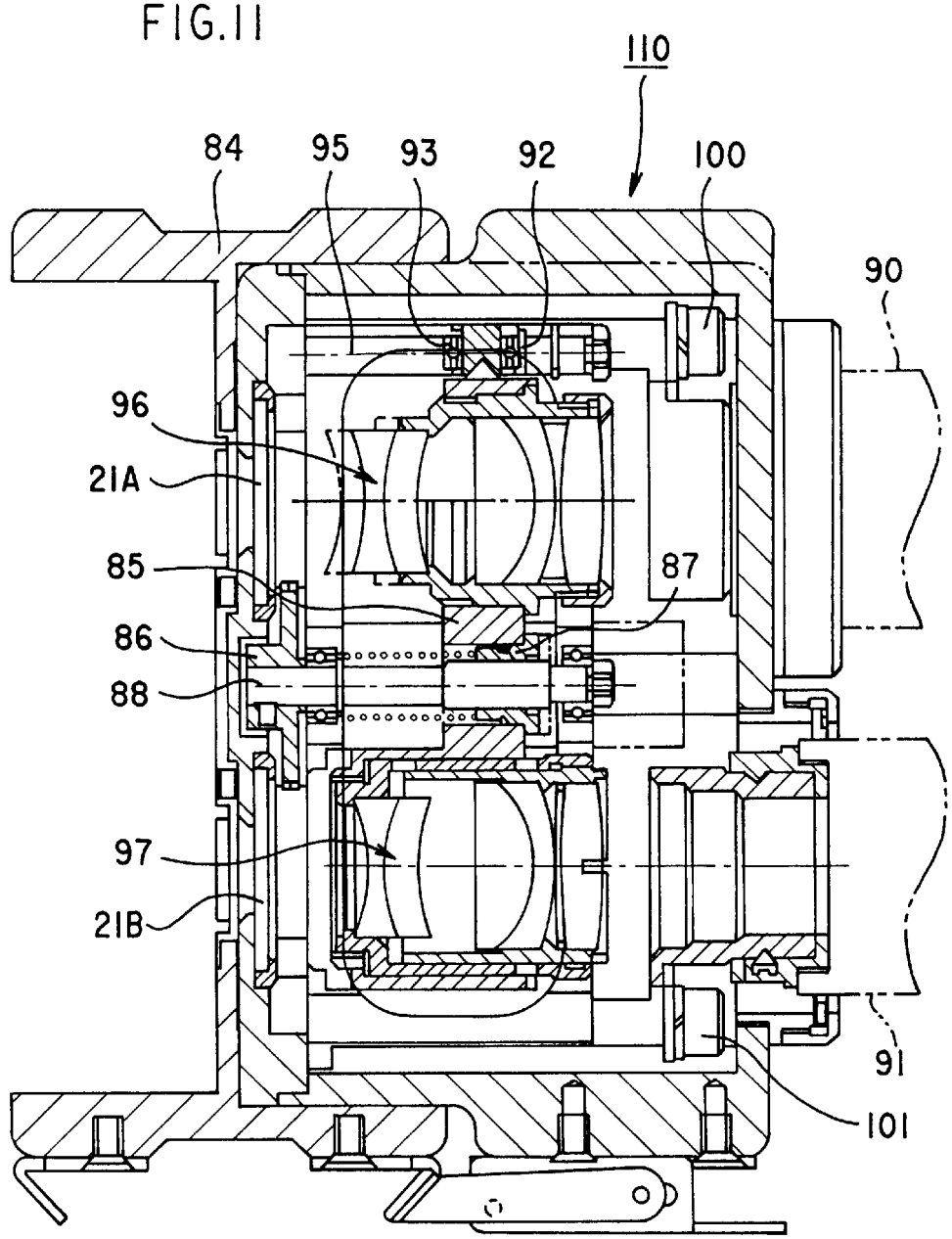
FIG. 11 is a sectional drawing of a camera adaptor of the stereoscopic endoscope of FIG. 2(a).

As shown in FIG. 11, at the observation part 3, a pair of first and second camera heads 90 and 91 which optically connect with a pair of observation optical systems 155, 156, respectively, are mounted together through a common camera adaptor 110. The camera adaptor 110 is attached to the third cover 80 of the observation part 3 through a connection adaptor 84. In addition, the camera head which has a CCD is also connected to the observation optical system 157 (see FIG. 14).

Two adapter image formation optical systems 96 and 97 are provided in the housing of the camera adaptor 110, correspond to the pair of observation optical systems 155, 156, respectively, and are held by a common movable image formation lens frame 85. The image formation lens frame 85 meshes with a transfer shaft 88, such as a worm shaft (screw shaft), to rotate, through a binding member 87. The worm shaft 88 is prolonged so that the center part of the image formation lens frame 85 may almost be penetrated and the image formation lens frame 85 can be partially supported by the meshing.

Figure 12:
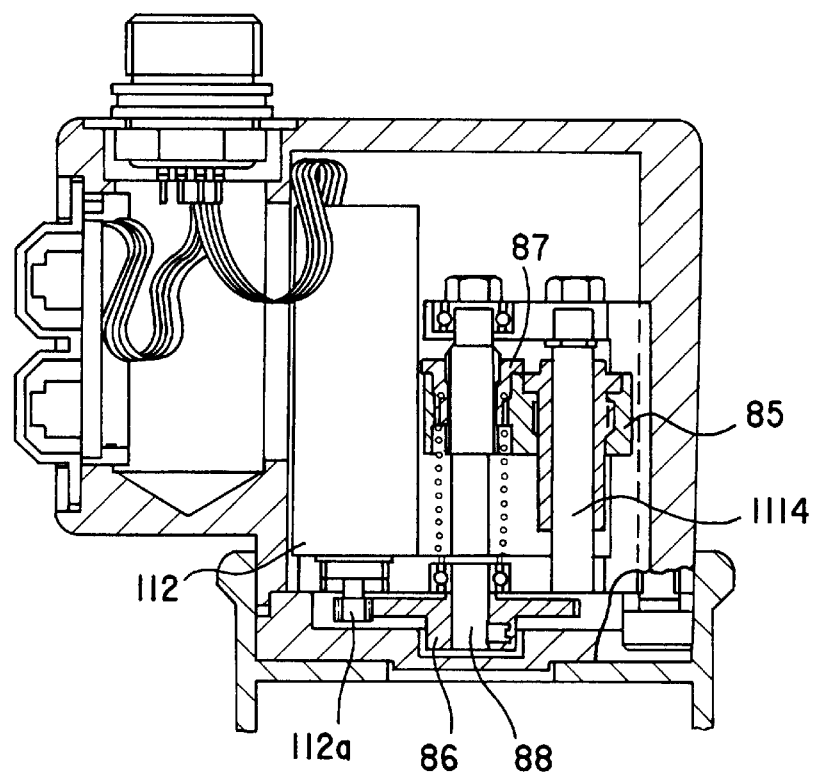
FIG. 12 is a sectional drawing illustrating the internal composition of a worm shaft periphery of a camera adaptor.

Moreover, as shown in FIG. 12, a rotation prevention shaft 114, which prevents rotation of the image formation lens frame 85 accompanied by rotation of the worm shaft 88, penetrates the circumference part of the image formation lens frame 85. Therefore, when the worm shaft 88 rotates, the image formation lens frame 85 will move in the direction of the optical axis, without rotating. The worm shaft 88 is integrally fixed to a spur gear 86, and the spur gear 86 is meshed with rotation axis 112a of a motor 112 (see FIG. 12). If the motor 112 actuates and rotation axis 112a rotates, the worm shaft 88 will rotate through the spur gear 86, and the image formation lens frame 85 will move in the direction of the optical axis.

Figure 13:
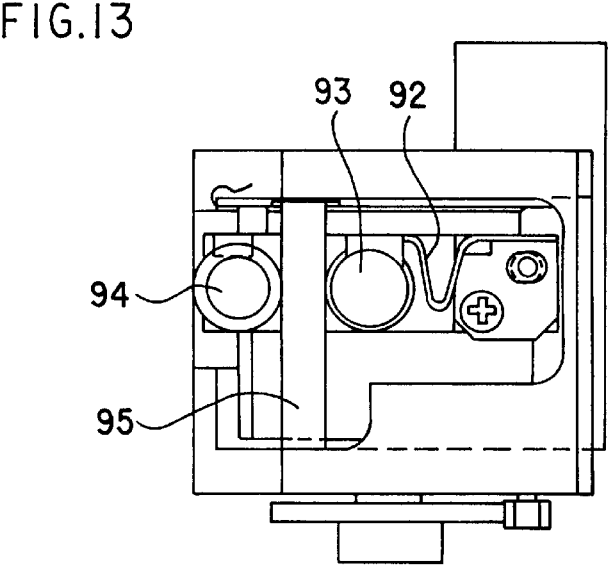
FIG. 13 is a sectional drawing illustrating the internal composition of a guide shaft and the circumference edge of a camera adaptor.

Moreover, a rattle prevention means is provided to the image formation lens frame 85 to prevent the image formation lens frame 85 from rattling in the rotation direction when the rotation prevention shaft 114 rattles or when the image formation lens frame 85 is moved in the direction of the optical axis and carries out a focus. As shown in FIGS. 11 and 13, the rattle prevention means consists of a guide axis 95 which leads the movement of the image formation lens frame 85 in the direction of the optical axis, a flat spring 92 and a pair of rotation rollers 93 and 94 mounted in the image formation lens frame 85. The pair of rotation rollers 93 and 94 are pushed and applied by the guide shaft 95 according to the power of the flat spring 92. Each of the rotation rollers 93 and 94 has a bearing means built-in, which enables them to rotate and move along the guide shaft 95 in the direction of the optical axis. That is, the rotation rollers 93 and 94 are pushed to the guide shaft 95 with the rotation direction of the image formation lens frame 85 according to the power of the flat spring 92. Thereby, the rotation rollers 93 and 94 and the integral image formation lens frame 85 are prevented from rattling in the rotation direction. In addition, adjusting screws 100, 101 control the positioning of the camera head 90, 91 in the XY plane, thereby centering the optical systems 96 and 97.

When observing an affected region site in a living body, using the stereoscopic vision endoscope system which is composed above, the illumination light supplied to the observation part 3 through the light source light guide cables and the light guide connectors 82, 82 from the light source is transmitted through the light guide 35 and is irradiated from the end of the insertion part 2 to the affected region site which is a photographed object.

On the other hand, after the reflected light from an affected region site is transmitted to each of the object optical systems 60, 61, and 62, it is transmitted through the transmission optical system 52 to the observation part 3 side. The light transmitted through the transmission optical system 52 from the first object optical system 60 moves through the edge part opening 53b of the connection member 53 and an internal hole 13 of the connector 40a of the holder 40. After it is reflected by the first reflecting surface 10a and the second reflection surface 10b of the first prism 10, it is lead to the image formation optical system 22 (see FIG. 8). After the light led to the image formation optical system 22 forms an image on an formation surface 141 in front of the enlargement optical system 20, it forms an afocal light and is then led to the adapter image formation optical system 96 from a lens cover 21A of the camera adaptor 110. Then, it is led into the camera head 90 and an image is formed again in an image formation CCD.

Similarly, the light transmitted through the transmission optical system 52 from the second optical system 61, after being reflected by the first reflecting surface 11a and the second reflecting surface 11b of the second prism 11 (see FIG. 8), is led to the image formation optical system 22. After the light led to the image formation optical system 22 forms an image on a formation surface 141 in front of the enlargement optical system 20, it forms an afocal light and is then led to the adapter image formation optical system 97 from a lens cover 21B of the camera adaptor 110. Then, it is led into the camera head 91 and an image is formed again in an image formation CCD. Therefore a stereoscopic image of an affected region site is projected clearly on the monitor which is connected the camera heads 90 and 91.

On the other hand, the light transmitted through the transmission optical system 52 from the third object optical system 62 moves through an edge part opening 53b of the connection member 53, and the internal hole 13 of connector 40a of the holder 40, and permeates the single substance image formation optical system 14, and then goes to the prism 16. The light led to the prism 16 is then led to the single enlargement optical system 157, after being reflected by first reflecting surface 16a and the second reflecting surface 16b of the prism 16 (see FIG. 7). After forming an image on an image formation surface 72, it forms an afocal light by the single observation optical system 157, and is then led into a camera head, and an image is formed again in an image formation CCD by the single solid mage pick-up element.

Moreover, for example, when a display mode is changed at the monitor side during a stereoscopic observation using the first and the second object optical systems 60 and 61, it is possible to switch an observation using the third optical system 62 from the stereoscopic observation using the first and second optical systems 60 and 61. Or, the observation using the third object optical system 62 can be simultaneously performed with the stereoscopic observation using the first and the second optical systems 60 and 61. Therefore, when an operator performs a treatment of the affected region site, observing a narrow visual field range three dimensionally using the first and the second optical systems 60 and 61, and an operator wants to observe the treatment tools and the entire position relationship outside the visual field, the treatment tools and the entire position relationship outside the visual filed can be observed through the third object optical system 62 and the single enlargement optical system 157, only by changing a display mode, without moving the lens of the pair of observation optical systems 155, 156 and the endoscope itself if the third object optical system 62 is set up for a wide-angle view. That is, both a narrow angle as well as a wide-angle can be used properly and an exact and efficient operation can be performed without moving a lens or the endoscope itself.

As explained above, according to this invention, a stereoscopic endoscope system can use a visual field range properly, wide-angle and narrow angle, without moving a lens or the endoscope itself.

What is claimed is:

1. A stereoscopic endoscope system which includes a combined system of a stereoscopic vision endoscope unit and a camera unit, said system comprising:

an insertion part and an observation part;

said insertion part including an objective lens and a relay lens in order from an object side, said objective lens having a pair of first and second optical systems which are arranged in parallel in an insertion direction, and a third optical system arranged in the insertion direction, said first and second optical systems being optical systems for a stereoscopic vision observation, said third optical system having a viewing angle larger than that of the first and second optical systems for observing a wider range than that of the stereoscopic vision observation; and said relay lens being arranged on the camera unit side of the objective lens.

2. The stereoscopic endoscope system as recited in claim 1, wherein the first optical system is inserted and fixed to a first tubular member, the second optical system is inserted and fixed to a second tubular member and the third optical system is inserted and fixed to a thirrd tubular member.

3. The stereoscopic endoscope system as recited in claim 2, wherein the first to third optical systems are positioned by a position regulation member which supports both ends of the first to third optical systems at the object and the camera sides thereof, and the position regulation member is inserted and fixed to a fourth tubular member.

4. A stereoscopic endoscope system as recited in claim 1, wherein said observation part includes an image formation optical system and an enlargement optical system, said image formation optical system and said enlargement optical system being arranged in the camera side of the relay lens, said image formation optical system and said enlargement optical system includes a pair of image formation optical systems and a pair of enlargement optical systems, corresponding to the pair of the first and second optical systems, and a single image formation optical system and a single enlargement optical system, corresponding to the third optical system, are arranged in the camera side of the relay lens.

5. The stereoscopic endoscope as recited in claim 4, wherein the pair of the image formation optical systems and the pair of the enlargement optical systems, and the single enlargement optical system are respectively inserted in a lens frame, wherein the lens frame has an adjusting mechanism so that a position can be adjusted in a direction perpendicular to a direction of an optical axis.

6. The stereoscopic endoscope system as recited in claim 5, wherein said adjusting mechanism adjusts the optical axis by screwing a plurality of screws into a v-shaped slot provided on a periphery of the lens frame.

7. The stereoscopic endoscope system as recited in claim 4, wherein said observation part has two parallelogram prisms arranged to correspond to the pair of first and second optical systems, respectively, to extend a distance between optical paths of the first and second optical systems on the camera side of the relay lens, and the image formation optical system and the enlargement optical system are arranged on the camera side of the parallelogram prism.

8. The stereoscopic endoscope system as recited in claim 7, wherein the single image formation optical system is integrally arranged in a space which is formed by cutting out a marginal part of each of the two parallelogram prisms, and a holder is arranged to fix the two parallelogram prisms and the single image formation optical system together, and the holder has an adjusting mechanism so that a position can be adjusted in a surface vertical to the insertion direction which is the direction of optical axis.

9. The stereoscopic endoscope system as recited in claim 4, wherein the camera unit includes an adapter and a camera head, wherein the adapter includes a pair of adapter image formation optical systems corresponding to the pair of enlargement optical systems and a single adapter image formation optical system corresponding to the single enlargement optical system.

10. The stereoscopic endoscope system as recited in claim 9, wherein said camera head includes a pair of solid image pick-up elements, corresponding to the pair of the adapter image formation optical systems, and a solid image pick-up element corresponding to the single adapter image formation optical system.

11. The stereoscopic endoscope system as recited in claim 9, wherein the pair of the adapter image formation optical systems is inserted into a image formation lens frame, wherein the image formation lens frame includes a focus moving mechanism for focus adjustments, and when the image formation lens frame moves, the pair of the adapter image formation optical systems moves simultaneously.

12. The stereoscopic endoscope system as recited in claim 11, wherein the focus moving mechanism of the pair of the adapter image formation optical systems includes a worm shaft which converts rotary motion into movement in the direction of an optical axis, and a rotation prevention shaft which prevents rotation of the image formation lens frame in connection with the rotation of the worm shaft.

13. The stereoscopic endoscope system as recited in claim 11, wherein said focus moving mechanism of the pair of the adapter image formation optical systems has a guide shaft provided along a transfer shaft and a rotation roller, which rotates and moves in contact with the guide shaft, arranged in the image formation lens frame, in order to prevent rotation resulting from ricketiness of the rotation prevention shaft and the image formation lens frame.

14. The stereoscopic endoscope system as recited in claim 13, wherein the rotation roller is pressed down on the guide shaft by the force of a spring.

15. A stereoscopic endoscope system as recited in claim 1, wherein the stereoscopic vision endoscope unit further includes a light guide, wherein the light guide is built in and arranged in a space between an outer side sheath of the stereoscopic vision endoscope unit and the objective and relay lenses, which extends from the object side end of the objective lens to the observation part.

16. The stereoscopic endoscope system as recited in claim 15, wherein an end of said light guide is ramified into a pair in the observation part.

17. The stereoscopic endoscope system as recited in claim 15, wherein said system further includes a pair of light source light guide cables which connect the observation part and a light source, and the pair of light source light guide cables are detachably mounted to the light guide.

18. The stereoscopic endoscope system as recited in claim 1, wherein the light guide is built in a space between the outer side sheath of the stereoscopic vision endoscope unit and the objective and the relay lenses, in a position near the third optical system, which extends from the object side end of the objective lens to the observation part.

19. A stereoscopic endoscope system as recited in claim 1, wherein the relay lens includes a single image transmitting optical system that transmit a plurality of images formed by the first, second and third optical systems.

20. A method for adjusting or assembling a stereoscopic endoscope system, comprising at least the following steps:

(A) fixing the position of a plurality of objective lenses in an insertion part, and a relay lens;

(B) forming a stereoscopic endoscope unit by combining an observation part with the insertion part;

(C) fixing the position of an image formation optical system and an enlargement optical system built-in the observation part;

(D) combining a camera unit with the stereoscopic endoscope unit; and (E) fixing the position of an adapter and a camera head built-in in the camera unit.

21. A method for adjusting or assembling a stereoscopic endoscope system as recited in claim 20, wherein said step (A) includes the following steps, respectively inserting a plurality of the objective lenses in a plurality of object tubular members and fixing it, the plurality of the optical tubular members fixes the relative position of a plurality of the object optical systems by a pair of position regulation members which supports the both ends of the object and the camera thereof, inserting the position regulation member into an insertion tubular member and fixing it, fixing the relay lens in contact with the camera side of the insertion tubular member;

said step B comprising of the following step at least, combining the observation part with the insertion part, and fixing a rotation position centering around the insertion direction;

said step C comprising of the following step at least, performing the positioning control of the direction of an optical axis of the image formation optical system and positioning control in surface vertical to an optical axis, and fixing;

said step D comprising of the following step at least, combining a camera unit with the solid endoscope unit, and fixing a rotation position centering around an insertion direction;

said step E comprising of the following step at least, fixing by performing the positioning control of the direction of an optical axis of the adapter and the camera head, and positioning control in surface vertical to an optical axis.

* * * * *